US009125806B2

(12) United States Patent
Mailland et al.

(10) Patent No.: US 9,125,806 B2
(45) Date of Patent: Sep. 8, 2015

(54) COMPOSITIONS WITH ENHANCED ELASTICIZING ACTIVITY

(75) Inventors: Federico Mailland, Milan (IT); Paolo Mascarucci, Lugano (CH); Emanuela Mura, Como (IT)

(73) Assignee: POLICHEM SA, Luxembourg (LU)

( * ) Notice: Subject to any disclaimer, the term of this patent is extended or adjusted under 35 U.S.C. 154(b) by 528 days.

(21) Appl. No.: 12/310,032

(22) PCT Filed: Apr. 18, 2007

(86) PCT No.: PCT/EP2007/053793
§ 371 (c)(1),
(2), (4) Date: Feb. 6, 2009

(87) PCT Pub. No.: WO2008/017521
PCT Pub. Date: Feb. 14, 2008

(65) Prior Publication Data
US 2009/0291931 A1 Nov. 26, 2009

(30) Foreign Application Priority Data
Aug. 9, 2006 (EP) .................................... 06118649

(51) Int. Cl.
A61K 31/095 (2006.01)
A61K 31/23 (2006.01)
A61K 8/44 (2006.01)
A61K 9/00 (2006.01)
A61K 31/198 (2006.01)
A61K 31/426 (2006.01)
A61K 47/12 (2006.01)
A61K 47/20 (2006.01)
A61K 47/22 (2006.01)
A61K 47/44 (2006.01)

(52) U.S. Cl.
CPC ............. *A61K 9/0034* (2013.01); *A61K 31/095* (2013.01); *A61K 31/198* (2013.01); *A61K 31/23* (2013.01); *A61K 31/426* (2013.01); *A61K 47/12* (2013.01); *A61K 47/20* (2013.01); *A61K 47/22* (2013.01); *A61K 47/44* (2013.01)

(58) Field of Classification Search
None
See application file for complete search history.

(56) References Cited

U.S. PATENT DOCUMENTS 6,077,520 A * 6/2000 Tominaga ...................... 424/401
6,153,649 A * 11/2000 Maignan ........................ 514/557
6,821,524 B2 * 11/2004 Marini ............................ 424/401
2004/0265268 A1 * 12/2004 Jain ............................. 424/85.1
2005/0266064 A1 * 12/2005 McCarthy ..................... 424/450
2006/0134155 A1 * 6/2006 Dryer et al. ................... 424/401

FOREIGN PATENT DOCUMENTS

| EP | 576287 A1 | * 12/1993 |
| EP | 1719502 | 11/2006 |
| WO | 95/34280 | 12/1995 |
| WO | 2006/050951 | 5/2006 |
| WO | WO2006045364 | 5/2006 |
| WO | WO2006045428 | 5/2006 |
| WO | WO2006045584 | 5/2006 |

OTHER PUBLICATIONS

Lovekamp-Swan, T., Davis, B.D. Mechanisms of Phthalate Ester Toxicity in the Femal Reproductive System. Environmental Health Perspectives 111 (2003), 139-145.*
Goel, G., Makkar, H.P.S., Francis, G., Becker, K. Phorbol Esters: Structure, Biological Activity, and Toxicity in Animals. International Journal of Toxicology 26 (2007), 279-288.*
Ashland University, Esters in Nature and Society. Downloaded from http://personal.ashland.edu/~bmohney/ket_scholars/esters.html on May 20, 2011.*
Sahu, S. C., Dual Role of Organosulfur Compounds in Foods: A Review. Environ. Carcino. & Ecotox. Revs. C20(1) (2002), 61-76.*
Jover, E., Moldovan, Z., Bayona, J.M. Complete characterization of lanolin steryl esters by sub-ambient pressure gas chromatography-mass spectrometry in the electron impact and chemical ionization modes. Journal of Chromatography A, 970, (2002) 249-258.*
Labrecque, M., Eason, E., Marcoux, S., Lemieux, F.,.Pinault, J-J., Feldman, P., Laperriere, L. Randomized controlled trial of prevention of perineal trauma by perineal massage during pregnancy. Am. J. Obstet. Gynecol, (1999), 593-600.*
Gentz, B.A. Alternative Therapies for the Management of Pain in Labor and Delivery. Clinical Obstetrics and Gynecology 44 (4), 2001, 704-732.*
McDowell, R.S., Dennis, M.S., Louie, A., Shuster, M., Mulkerrin, M.G., Lazarus, R.A. Mambin, a Potent Glucoprotein IIb-IIIa Antagonist and Platelet Aggregation Inhibitor Structurally Related to the Short Neurotoxins. Biochemistry 1992, 31, 4766-4772.*
Wikipedia entry for skunk: http://en.wikipedia.org/wiki/Skunk, downloaded from the internet on May 20, 2011.*
Corzo-Martinez, M. Corzo, N., Villamiel, M. Biological properties of onions and garlic. Trends in Food Science and Technology 2007, 18, 609-625.*

(Continued)

Primary Examiner — Frederick Krass
Assistant Examiner — Michael P Cohen
(74) Attorney, Agent, or Firm — Hueschen and Sage

(57) ABSTRACT

Compositions for improving the elasticity of the vagina and of the perineum during the last trimester of pregnancy, include combining a thiolated compound or mixture thereof with an ester of organic acid or mixture thereof. The compositions according to the present invention improve the elastic properties of the vaginal and/or perineal tissues in terms both of increased extensibility and faster elastic recovery. The compositions according to the present invention may decrease risk of trauma of perineal tissues during delivery, as well as risk of rectal or bladder incontinence as a post-partum short/medium/long term complication.

9 Claims, No Drawings

(56) References Cited

OTHER PUBLICATIONS

Lourdes Soler, Jaime Caiiellas, and Fulgencio Saura-Calixto. Oil Content and Fatty Acid Composition of Developing Almond Seeds. J. Agric. Food Chem. 1988, 36, 695-697.*

Michel Labrecque, Erica Eason, Sylvie Marcoux, Francois Lemieux, Jean-Jacques Pinault, Perle Feldman, and Louise Laperriere. Randomized controlled trial of prevention of perineal trauma by perineal massage during pregnancy. Am J Obstet Gynecol, Mar. 1999, pp. 593-600.*

Van der Walle, H. B., and V. M. Brunsveld. "Dermatitis in hairdressers.(I). The experience of the past 4 years." Contact Dermatitis 30.4 (1994): 217-221.*

P.Elsner, Dorothea Wilhelm, and H.I.Maibach. Mechanical properties of human forearm and vulvar skin. British Journal of Dermatology (1990) 122, 607-614.*

Beckmann, et al., *Birth*, 2006, 33, 159.

International Search Report for PCT/EP2007/053793 of Mar. 27, 2008.

* cited by examiner

COMPOSITIONS WITH ENHANCED ELASTICIZING ACTIVITY

This invention relates to compositions of thiolated compounds combined to esters of organic acids useful to enhance the elasticizing properties on vaginal and/or perineal tissues.

BACKGROUND OF THE INVENTION

In the art, thiolated compounds, both those provided with free SH groups, and those with the S— atom blocked by a functional group, have the capability to decrease the rigidity of protein structures, by breaking the disulphur bonds, resulting in increasing the extensibility of the protein molecule. This result is achieved by acting both on ternary and quaternary structure, without affecting the primary and secondary ones, and therefore is reversible. This action is very well known and it is applied in two large fields, like in human therapy of bronchitis, to decrease sputum viscosity and improve bronchial and tracheal clearance both in acute and chronic bronchitis; on the other hand, it is applied by cosmetic industry to improve skin softness in subjects with wrinkles or striae. In fact, the structure of keratin, the main constituent of the skin, is rich of disulphur bonds as a result of interactions between two non contiguous molecules of cisteine, in the aminoacidic chain. Same is to be said for sputum, which constituents are rich of disulphur bonds. The breaking of the disulphur bond, by reducing the —SS— bridge to two —SH free groups, allows the protein to extend, by loosing the rigidity due to the covalent bond. On the other hand, this phenomenon is reversible, in fact the two SH free groups may further interact and form an —SS— bridge.

Esters of alcohols and organic acids are known in the art and used as skin care and nurturing for the prevention and reduction of stretch marks. They substantially act while keeping essential emollients actively softening and elasticizing. Triglycerides are esters of glycerol, that are physiologically present in the animal and vegetable tissues. Those esters are composed of organic fatty acids, with a Carbon atom chain varying between 6 to 18 Carbon atoms, they may be saturated or unsaturated, mainly mono-, di- or tri-unsaturated. The chain length and the presence of double bonds affect the melting point of the fatty acids and of their esters. The lowering of the melting point confers to these compounds a semisolid or liquid state that is useful for their emollient and humectant properties. Cholesterides are esters of cholesterol and organic fatty acids, also present in nature, mostly in fats and nervous tissues of animals. They also are used in the preparation of creams and ointments due to their emollient properties. Phytosterol esters are the correspondent in the vegetables, where the sterol components of the ingredient vegetable oil phytosterol esters are beta-sitosterol, campesterol, and stigmasterol. These components of vegetable oil phytosterol esters already are present as ingredients in cosmetics as skin care products for their emollient properties, thus they have a similar intended use to cholesterides and triglycerides. Fatty acids that enter in the composition of esters with sterols are also varying between 6 to 18 Carbon atoms, they may be saturated or unsaturated, mainly mono-, di- or tri-unsaturated fatty acids. Esters of alcohols and organic acids may be synthetic, such as isopropyl-miristate and isopropyl palmitate. Isopropyl-myristate is the ester of isopropyl alcohol and myristic acid, a saturated C-14 fatty acid: it is widely used both in cosmetic and pharmaceutical industry, also for vaginal preparations. The compositions object of the present invention contain at least a thiolated compound and an ester of organic acid which act synergistically in improving tissue elasticity in terms of increased both extensibility and elastic recovery. This feature is important to increase elasticity of the distal portion of the vagina and of the perineal tissues during the last trimester of pregnancy. Spontaneous delivery is often accompanied by lacerations of the perineal tissues due to excessive extension during the expulsive phase. Short-medium term complications are often pain, dyspareunia and urinary incontinence in 30-50% of women (Lukacz E S et al. *Obst Gynecol.* 2006—Olsen L O, et al *Obstet. Gynecol.* 1997).

The practice to episiotomy may decrease the spontaneous lacerations in terms of both rate and severity of lacerations, but it is not devoid of complications, like dyspareunia and rectal incontinence of puerperal women. According to a recent systematic evidence review, although episiotomy is performed in approximately 30-35% of vaginal birth in the United States, no statistically significant difference were reported for severe vaginal or perineal trauma, dyspareunia or urinary incontinence (ACOG Practice Bulletin. Episiotomy. Clinical Management Guidelines for *Obstet. Gynecol.* 2006).

Perineal massage during the last weeks of pregnancy is a practice known in the art to prepare the tissues to the increased request of extension during spontaneous delivery. Ten-fifteen minutes massage is performed during the last 6-8 weeks before delivery, mostly daily or tri-weekly. Almond oil is used as a lubricant. The usefulness of this practice is controversial: according to the literature, the practice of the perineal massage is capable to improve the extensibility of the perineal tissues, by significantly reducing the incidence of trauma requiring suturing and number of episiotomy in woman without previous vaginal birth, but no differences were seen in the incidence of $1^{st}$ or $2^{nd}$ degree perineal tears or $3^{rd}$ to $4^{th}$ degree perineal trauma compared to women not practicing the perineal massage (Beckmann M M et al. *Birth* 2006).

It has now been shown that compositions containing at least a thiolated compound and an ester of organic acid and appropriate excipients improve the elasticity of the skin by a synergistic action of the two components, namely the thiolated compound and the ester of organic acid. Furthermore, the regular application of compositions containing at least a thiolated compound and an ester of organic acid and appropriate excipients is capable to increase the elastic properties of the distal part of the vagina and of the perineal tissues. The compositions are preferably in form of cream, ointment, gel or lotion, and are preferably topically applied by perineal massage, to improve penetration of the ingredients deeply into the perineal tissues, and to train the vaginal and perineal muscles to the expulsive phase of delivery as well.

The compositions contain at least a thiolated compound in a proportion ranging between 0.1 to 25 wt. %, preferably from 0.5 to 15 wt. %, more preferably from 1.0 to 10%, with respect to the total weight of the composition. The thiolated compound is preferably a sulphated aminoacid, more preferably a derivative of cysteine, most preferably a salt of carboxymethyl-cysteine. According to a preferred embodiment, said sulphated amino acid is selected from: 1-methionine, 1-cysteine, 1-cystine, taurine, 4-thiazolidinecarboxylic acid, carboximethylcisteine and/or methylsulphonylmethane, or a physiologically acceptable salt thereof.

The compositions contain at least an ester of organic acid in a proportion ranging between 1 to 95 wt. %, preferably from 5 to 70 wt. %, more preferably from 10 to 45%, with respect to the total weight of the composition. The ester of organic acid is preferably an ester of glycerol or an ester of animal or vegetable sterol, such as cholesterol, or a mixture thereof.

The organic acid contains from 2 to 30 carbon atoms, preferably from 6 to 18 carbon atoms, more preferably from 12 to 18 carbon atoms. The organic acid is saturated or unsaturated.

The compositions will be prepared according to conventional techniques, and may include compatible excipients and pharmaceutically acceptable carriers, e.g. ionizing agents, antioxidant agents, chelating agents, moisturizing agents, decongestant agents, disinfectant and/or antimicrobial agents, flavoring and colorants.

The compositions may also contain, in combination, other active principles with complementary or, in any case, useful activity. Examples of these compositions prepared according to the present invention include: cream, ointment, gel, lotion or foam.

The pharmaceutical compositions and the uses of the present invention will now be more fully described by the following examples. It should, however, be noted that such examples are given by way of illustration and not of limitation.

EXAMPLE 1

A lipogel (=homogeneous hydrophobic ointment) formulation having the following w/w % composition was prepared:

| | | |
|---|---|---|
| 1) Lysine Carboxymethyl Cysteinate[1] | 5.00% |
| 2) Polyglyceryl-3 Beeswax[2] | 7.50% |
| 3) *Prunus amygdalus* var. *dulcis*[3] | 12.00% |
| 4) Tocopherol, Lecithin, Ascorbyl palmitate, Citric acid[4] | 0.05% |
| 5) Petrolatum[5] | 15.00% |
| 6) Hydrogenated castor oil[6] | 2.00% |
| 7) Paraffinun liquidum[7] | q.s. to 100.00% |

[1]Elastocell ®;
[2]Cera Bellina (hydrophilic derivative of beeswax in which the free fatty acids have been converted to polyglycerol esters);
[3]Sweet Almond Oil(containing glycerides from oleic acid for about 65%).;
[4]Aperoxid TLA;
[5]White Soft Paraffin;
[6]Cutina ® HR Powder (consisting mainly of triglycerides of hydroxystearic acid (C18));
[7]Pharma 55

Paraffinun liquidum, Polyglyceryl-3 Beeswax, Prunus amygdalus var. dulcis, Aperoxid TLA and Petrolatum were mixed in a turboemulsor and heated at 70° C. When the mass was melted, Hydrogenated castor oil was added under moderate stirring until complete dispersion.

The melted mass was then cooled at 45° C. and Lysine Carboxymethyl Cysteinate was added under stirring until a homogeneous gel was obtained.

The obtained gel contains 21.50% of esters according to the invention; it is ivory and homogeneous in appearance.

EXAMPLE 2

A lipogel (=homogeneous hydrophobic ointment) formulation having the following w/w % composition was prepared:

| | |
|---|---|
| 1) Lysine Carboxymethyl Cysteinate | 7.50% |
| 2) Polyglyceryl-3 Beeswax | 5.00% |
| 3) Acetylated Lanolin* | 2.00% |
| 4) Tocopherol, Lecithin, Ascorbyl palmitate, Citric acid | 0.05% |
| 5) Petrolatum | 38.50% |
| 6) Paraffinun liquidum | 14.00% |
| 7) Hydrogenated castor oil | 3.00% |
| 8) Soybean oil** | q.s. to 100.00% |

*Modulan ™Lanolin Derivative (Noveon) Acetylated Lanolin Alcohol;
**Consisting in glycerides of linoleic acid (50-57%); linolenic acid (5-10%); oleic acid (17-26%); palmitic acid (9-13%); and stearic acid (3-6%).

The obtained gel contains 39.95% of esters according to the invention

The formulation was prepared by using the same method described for Example 1.

EXAMPLE 3

A lipogel (=homogeneous hydrophobic ointment) formulation having the following w/w % composition was prepared:

| | |
|---|---|
| 1) Lysine Carboxymethyl Cysteinate | 5.00% |
| 2) Polyglyceryl-3 Beeswax | 5.00% |
| 3) *Prunus amygdalus* var. *dulcis* | 12.00% |
| 4) Tocopherol, Lecithin, Ascorbyl palmitate, Citric acid | 0.10% |
| 5) Petrolatum | 15.00% |
| 6) Phytosterol ester* | 15.00% |
| 7) Hydrogenated castor oil | 3.50% |
| 8) Silica | 1.50% |
| 9) Paraffinun liquidum | q.s. to 100.00 |

*Vegapure (Cognis)

The obtained gel contains 35.5% of esters according to the invention

The formulation was prepared by using the same method described for Example 1.

EXAMPLE 4

A lipogel (=homogeneous hydrophobic ointment) formulation having the following w/w % composition was prepared:

| | |
|---|---|
| 1) Lysine Carboxymethyl Cysteinate | 5.00% |
| 2) Polyglyceryl-3 Beeswax | 7.50% |
| 3) *Prunus amygdalus* var. *dulcis* | 7.00% |
| 4) Isopropyl Myristate* | 5.00% |
| 5) Tocopherol, Lecithin, Ascorbyl palmitate, Citric acid | 0.10% |
| 6) Petrolatum | 15.00% |
| 7) Hydrogenated castor oil | 4.50% |
| 8) Silica | 1.50% |
| 9) Paraffinun liquidum | q.s. to 100.00% |

*Crodamol IPM (Croda, ester of isopropyl alcohol and myristic acid, saturated C14 fatty acid)

The obtained gel contains 24.00% of esters according to the invention

The formulation was prepared by using the same method described for Example 1.

EXAMPLE 5

A lipogel (=homogeneous hydrophobic ointment) formulation having the following w/w % composition was prepared:

| | |
|---|---|
| 1) L-Methionine | 5.00% |
| 2) Synthetic Beeswax* | 8.50% |
| 3) *Prunus amygdalus* var. *dulcis* | 12.00% |

-continued

| | | |
|---|---|---|
| 4) | Tocopherol, Lecithin, Ascorbyl palmitate, Citric acid | 0.05% |
| 5) | Petrolatum | 15.00% |
| 6) | Hydrogenated castor oil | 4.00% |
| 7) | Silica | 2.50% |
| 8) | Neem oil** | 1.00% |
| 9) | Sesame seed oil*** | 2.50% |
| 10) | Paraffinun liquidum | q.s. to 100.00% |

*Syncrowax BB4 (Croda)
**Contains a mixture of tryglicerides of linoleic, oleic, palmitic and stearic acids
***Contains glycerides of arachidic acid (0.8%), linoleic acid (40.4%), oleic acid (45.4%), palmitic acid (9.1%), and stearic acid (4.3%)

The obtained gel contains 27.50% of esters according to the invention

The formulation was prepared by using the same method described for Example 1.

EXAMPLE 6

A lipogel (=homogeneous hydrophobic ointment) formulation having the following w/w % composition was prepared:

| | | |
|---|---|---|
| 1) | Methylsulfonyl methane | 5.00% |
| 2) | Synthetic Beeswax | 5.00% |
| 3) | *Prunus amygdalus* var. *dulcis* | 12.00% |
| 4) | Tocopherol, Lecithin, Ascorbyl palmitate, Citric acid | 0.10% |
| 5) | Petrolatum | 15.00% |
| 6) | Hydrogenated vegetable oil* | 3.50% |
| 7) | Silica | 1.50% |
| 8) | Paraffinun liquidum | q.s. to 100.00% |

*CEGESOFT ® HF62 (Cognis, contains a mixture of C16-C24 triglycerides)

The obtained gel contains 20.50% of esters according to the invention

The formulation was prepared by using the same method described for Example 1.

EXAMPLE 7

A lipogel (=homogeneous hydrophobic ointment) formulation having the following w/w % composition was prepared:

| | | |
|---|---|---|
| 1) | Lysine Carboxymethyl Cysteinate | 5.00% |
| 2) | Synthetic Beeswax | 5.00% |
| 3) | *Prunus amygdalus* var. *dulcis* | 6.00% |
| 4) | Tocopherol, Lecithin, Ascorbyl palmitate, Citric acid | 0.10% |
| 5) | Petrolatum | 15.00% |
| 6) | Lanolin Alcohol* | 3.50% |
| 7) | Lanolin USP** | 6.00% |
| 8) | Silica | 1.50% |
| 9) | Paraffinun liquidum | q.s. to 100.00% |

*Super Hartolan (Croda, cholesterol-rich solid fraction of pharmaceutical grade lanolin);
**Medilan ™(Croda, containing a mixture of cholesterol and the esters of several fatty acids The obtained gel contains 20.50% of esters according to the invention The formulation was prepared by using the same method described for Example 1.

EXAMPLE 8

Comparative Clinical Test

A clinical study on healthy volunteers has been performed with the aim to investigate the skin elasticizing activity of 3 different compositions in acute testing, compared to a standard reference product consisting of white soft paraffin. Aim of the study was to compare the activity of a formulation containing a thiolated compound like a Carboxymethyl Cysteinate salt, and a mixture of esters of fatty acids and glycerol, with that of different formulations containing a thiolated compound alone or ester mixtures alone.

The volunteers were 21 women, aged between 24 and 55 years (mean 45 yrs). Each product has been randomly applied once, by a mild massage, on the volar surface of forearm. Plastoelasticity measurement were performed at baseline and 30 minutes after the application of each product by means of torsiometry measured by the Dermal Torque Meter (Dia-Stron LTD) as described in Sparavigna A, Setaro M, "Diagnostica non invasiva in dermatologia" a cura di Stefania Seidenari, EDRA Medical Publishing & New Media, Milano, 1998, pages 323-328.

This method employs the principle of torsion performed in vivo on a skin area, by an apparatus consisting in two concentric circles adhering to the skin through biadhesive tapes. The distance (1 mm) between the two circles limits the area undergoing the torsion. The inner circle, by rotating respect to the outer circle, exerts a constant torsion on the skin, that stops when the antagonistic effort of the skin balances the applied twisting moment (9 mNm). Duration of torsion is 1 sec. The apparatus measures the torsion angle θ resulting at the phase of mechanical solicitation and at its cessation as well.

The parameters measured by the a.m. technique were the elastic recovery and the skin elasticity measured as follows:
$U_e$: immediate extensibility
$U_f$: maximum extensibility
$U_v$: viscoelasticity
$U_r$: immediate elastic recovery
$U_r/U_e$: elastic recovery
$U_r/U_f$: skin elasticity
$U_v/U_e$: viscosity
$\tau_{on}$ and $\tau_{off}$ time constants on the curves "go on" and "go back"
The compositions employed were as follows:
Product 1: lipogel LPOL514, with composition according to the Example 1
Product 2: hydrogel LPOL513, with following w/w % composition:

| | | |
|---|---|---|
| 1) | Lysine Carboxymethyl Cysteinate[1] | 7.50% |
| 2) | Sodium Propylparaben | 0.04% |
| 3) | Sodium Methyllparaben | 0.37% |
| 4) | Imidazolidinyl Urea[2] | 0.20% |
| 5) | Disodium EDTA | 0.10% |
| 6) | Hydroxyethylcellulose[3] | 1.50% |
| 7) | Carragenine gel[4] | 5.00% |
| 8) | Citric acid | q.s. to pH 5.5 |
| 9) | Water | q.s. to 100.00% |

[1]Eastocell ®;
[2]Gram 1;
[3]Natrosol 250M;
[4]Seamollient

Product 3: hydrogel LPOL520, with following w/w % composition:

| | | |
|---|---|---|
| 1) | Hydrogenated soybean phosphatidylcholine[1] | 1.03% |
| 2) | Cholesterol USP | 0.26% |
| 3) | Butylated hydroxyanisole(BHA) | 0.10% |
| 4) | Ascorbic Acid | 7.10% |
| 5) | Glycerol | 5.00% |
| 6) | Disodium EDTA[2] | 0.10% |

-continued

| | | |
|---|---|---|
| 7) Sodium Methylparaben[3] | | 0.37% |
| 8) Sodium Propylparaben[4] | | 0.04% |
| 9) Imidazolidinyl Urea[5] | | 0.21% |
| 10) Hydroxyethylcellulose[6] | | 0.70% |
| 11) Xanthan gum[7] | | 1.00% |
| 12) Water | | q.s. to 100.00% |

[1]Lipoid S 100-3;
[2]Dissolvine NA-2;
[3]Nipagin M sodium;
[4]Nipasol M sodium;
[5]Gram 1;
[6]Natrosol 250M;
[7]Rhodigel Ultra Product 4: reference standard, with the following composition:

| | |
|---|---|
| 1) Petrolatum (=white soft paraffin) CAS n° 8009-03-08 | 100% |

The results are summarized in the following table 1:

TABLE 1 percent changes vs. baseline of torsiometric parameters 30 min after application of different investigational product or reference on the forearm skin of 21 healthy volunteers (Student's t test).

| Torsiometric parameter | Product 1 lipogel LPOL514 | Product 2 hydrogel LPOL513 | Product 3 vagigel LPOL520 | Product 4 Reference |
|---|---|---|---|---|
| Ur/Uf skin elasticity | +24% ** | +1% | −4% | +13% * |
| Ur/Ue elastic recovery | +23% *** | −1% | 0% | +13% * |

\* P < 0.05 vs baseline
\*\* P < 0.01 vs. baseline
\*\*\* P < 0.001 vs. baseline The results show a synergistic activity of the thiolated compound, contained in products 1 and 2, and the esters contained in the products 1, 3 and 4. As a matter of fact, when the two main components, thiolated compound and esters, where present alone, as in the product 2 (devoid of activity) or in the product 3 (devoid of activity), or in the product 4 (reference white soft paraffine, with a mild activity), the elasticizing activity was none or mild (not higher than 13%). On the contrary, when the thiolated compound and the esters were combined in the same formulation, as in product 1, the deriving elasticizing activity was robust (+24% on elasticity, and +23% on elastic recovery) and superior to that of esters alone. The resulting effect was synergistic, being superior for the combination to the sum of the two ingredients alone.

EXAMPLE 9

Comparative Clinical Test

A clinical study on pregnant women has been performed with the aim to investigate the elasticizing activity on perineal tissues and the capability to prevent traumatic injuries of the perineum during delivery, by regularly applying during the last two months of pregnancy a formulation according to the Example 3. The study was open label, compared versus an historical group.

Overall, 36 pregnant women were included in the study. All women were primipara (first pregnancy), none of them was at risk of caesarean parturition. The product was applied by performing a regular perineal massage daily since the beginning of the 30$^{th}$ week until spontaneous delivery. The application of the product (2-5 g) was done by moisturizing the perineum with the formulation, then by performing a gentle massage by circular movement on the labia and on the distal part of the vagina, for about 15 min.

The parameters assessed at the time of delivery were: extensibility and elastic recovery in a visual analogue scale (VAS) from 0 (none) to 100 (maximum), in the judgment of the gynecologist, percent of episiotomies, rate and grade of lacerations, adverse events and overall judgment of efficacy.

Results were as follows: extensibility was mean±SD 78.81±8.59, elastic recovery was 78.04±12.4, no episiotomy, 8.3% grade I lacerations, no grade II or III lacerations. The results relative to episiotomies and/or perineal lacerations were compared to an historical group of 425 spontaneous deliveries, including all the deliveries occurred in the same investigational centre during the whole 2004 period. The data are summarized in the following table 2.

TABLE 2 rate of episiotomies and lacerations during spontaneous delivery in the study group compared to an historical group of women

| | 2004 spontaneous deliveries (%, n = 425) | Study group (%, n = 36) |
|---|---|---|
| Episiotomies | 23.3 | 0 |
| Lacerations grade 1 (concern vulvovaginal mucous membrane and perineal skin) | 22.8 | 8.3 |
| Lacerations grade 2 (involve perineal muscles and perineal fascia) | 11.5 | 0 |
| Lacerations grade 3 (involve anal sphincter) | 0.8 | 0 |

It was concluded that the product was highly effective in improving elasticity of the perineum as well as in preventing traumatic complications on perineal tissues during delivery.

The invention claimed is:

1. A method for improving the elasticization of the vagina and of the perineum in pregnant women, which comprises administering to the perineum of a pregnant woman a topical composition comprising a synergistically effective combination of:
   a) carboxymethylcysteine or physiologically acceptable salts thereof, and
   b) a mixture of esters of fatty acids having from 16 to 18 carbon atoms and glycerol.

2. The method of claim 1, wherein component a) is present in an amount of from 0.1 to 25% by weight.

3. The method of claim 1, wherein component a) is present in an amount of from 0.5 to 15% by weight.

4. The method of claim 1, wherein component a) is present in an amount of from 1.0 to 10% by weight.

5. The method of claim 1, wherein the fatty acids are saturated or unsaturated.

6. The method of claim 1, wherein component b) is present in an amount of from 1.0 to 95% by weight.

7. The method of claim 1, wherein component b) is present in an amount of from 5 to 70% by weight.

8. The method of claim 1, wherein component b) is present in an amount of 10 to 45% by weight.

9. The method of claim 1, wherein the topical composition further comprises one or more pharmaceutically acceptable excipients.

* * * * *